United States Patent [19] [11] Patent Number: 4,736,630
Takahashi et al. [45] Date of Patent: Apr. 12, 1988

[54] APPARATUS AND METHOD FOR SENDING OUT AND RECEIVING ULTRASONIC WAVE SIGNALS

[75] Inventors: Fuminobu Takahashi, Katsuta; Kazunori Koga, Hitachi; Satoshi Ogura, Hitachi; Masahiro Koike, Hitachi, all of Japan

[73] Assignee: Hitachi, Ltd., Tokyo, Japan

[21] Appl. No.: 891,644

[22] Filed: Aug. 1, 1986

[30] Foreign Application Priority Data

Aug. 5, 1985 [JP] Japan ................. 60-172032
Aug. 22, 1985 [JP] Japan ................. 60-184604

[51] Int. Cl.$^4$ ............................................. G01N 29/00
[52] U.S. Cl. ......................................... 73/626; 73/628; 128/660
[58] Field of Search .................. 73/626, 628; 128/660

[56] References Cited

U.S. PATENT DOCUMENTS

| 4,412,316 | 10/1983 | Diepers ................ 73/626 |
| 4,472,973 | 9/1984 | Sugai et al. ............ 73/626 |
| 4,592,237 | 6/1986 | Ogura et al. ............ 73/628 |
| 4,597,292 | 7/1986 | Fujii et al. ............. 73/626 |
| 4,611,494 | 9/1986 | Uchiyama .............. 73/626 |

*Primary Examiner*—Stewart J. Levy
*Assistant Examiner*—Louis M. Arana
*Attorney, Agent, or Firm*—Fay, Sharpe, Beall, Fagan, Minnich & McKee

[57] ABSTRACT

An ultrasonic inspection apparatus and method in which a linear array of acoustic transmitters and receivers are disposed adjacent to a workpiece, and alternating potential source is connected to some of the acoustic transmitters to project a side lobe of an acoustic wave toward a specific zone of the workpiece. Thereafter, the connections between some of the acoustic transmitters and the potential source are automatically changed, to move the specific zone as many times as may be necessary to provided scanning of the workpiece.

29 Claims, 12 Drawing Sheets

APPARATUS AND METHOD FOR SENDING OUT AND RECEIVING ULTRASONIC WAVE SIGNALS

FIELD OF THE INVENTION

The present invention relates to an apparatus and a method for sending out and receiving ultrasonic wave signals. More especially, the present invention is useful for ultrasonic inspection in order to test and detect internal defects in a medium with nondestruction.

BACKGROUND OF THE INVENTION

It is one of the important things for the ultrasonic inspection that a direction of propagation of ultrasonic wave signals from a transducer to a medium, which is usually a material to be tested for internal defects, is set freely. For the purpose, various ideas have been proposed. Mori et al introduced ultrasonic inspection where it is possible to set freely the direction of propagation of ultrasonic wave signals in "Phased Array Type Ultrasonic Inspection Method and Equipment" in a magazine, *Journal of Institute of Japan Mechanical Engineers*, Vol. 87, No. 793, Dec., 1984. In the conventional system, a plurality of elements of a transducer, namely a plurality of ultrasonic wave signal sending means and/or receiving means, are placed adjacently each other. This is called a phased arrayed transducer. Each sending means is provided an electric pulse to send out ultrasonic wave signals at different times with respect to each other and in order. Then, the ultrasonic wave signals are sent out from the transducer and are propagated in a medium, on which the transducer is attached, with a predetermined refraction angle corresponding to the time interval of the application of the electric pulse between adjacent sending means. Ultrasonic wave signals which are reflected at interval defects or at a bottom surface of the medium are received by each of a plurality of receiving means which generate electric signals corresponding to the received ultrasonic wave signals. The electric signals generated by the plurality of receiving signals are added with a time interval, which is identical with that of the sending out of the ultrasonic wave signals. By the method, the ultrasonic wave signals are propagated with a predetermined refraction angle or are focused to a predetermined position corresponding to the time interval. However, it is needed to adjust each time interval between the plurality of sending means precisely. If it is embodied by some electrical delay circuits, the circuit will be very large in volume and very expensive. If it is embodied by some computer, it will be very expensive too.

SUMMARY OF THE INVENTION

In the present invention, some selected plural sending means that are corresponding to a refraction angle are provided an electric potential and/or the rest, not selected, plural sending means are provided an almost reverse phase, preferably perfectly reverse phase, of the electric potential. And some plural selected receiving means are connected to a processing means which processes electric signals generated by receiving means when the ultrasonic wave signals arrive and/or the rest, not selected, plural receiving means are connected to the processing means so as to provide the electric signals with reverse polarity. Then, in the present invention, by only selection of sending means are receiving means the refraction angle is set freely.

It is an object of the present invention to provide a small and not expensive apparatus and method for sending out and receiving ultrasonic wave signals.

It is an object of the present invention to provide an apparatus and using a plane transducer.

DETAILED DESCRIPTION

Figure 1A:
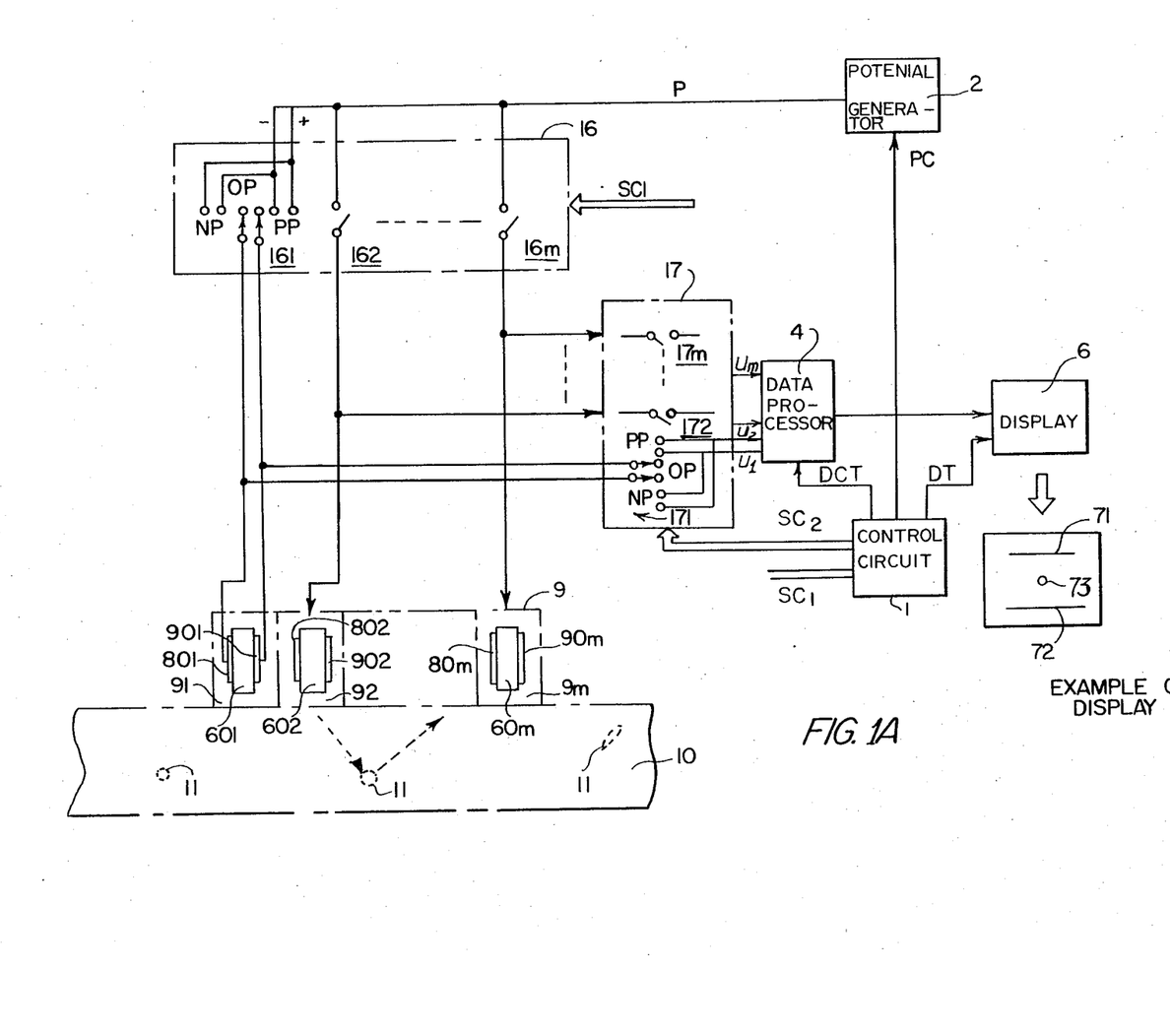
FIG. 1A shows a block diagram of the basic construction of the present invention.

FIG. 1A shows a block diagram of the basic construction of the present invention.

Figure 3A:
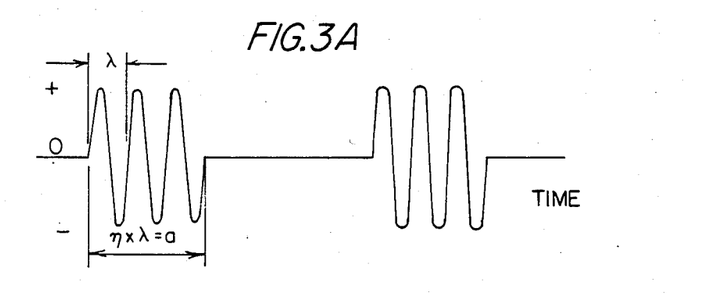
FIGS. 3A and 3B show an example of an electrical potential for wave generating the ultrasonic wave signals and an example of the generated ultrasonic wave signals.

A control circuit 1 generates some control signals. An electric potential generating means 2 generates an electric potential P having a predetermined wave and predetermined amplitude, an example of which is shown in FIG. 3A, according to a potential control signal PC given by the control circuit 1. Two connecting means 16 and 17 include m on-off switches 161, 162, ... 16m and 171, 172, 17m, respectively, each of which is turned on or off according to switch control signals Sc and SC given by the control circuit 1.

As shown about switches 161 and 171 in FIG. 1A, each switch is not only performing on and off operation, but also in capable to connect with reverse relation between input side and output side. Namely, when the contactors of the switches 161 and 171 are changed to terminals of off positions OP, the switches are off. When the contactors of the switches 161 and 171 are changed to terminals of positive positions PP, the switches are on and connect between input side and output side by a predetermined phase and a predetermined polarity. When the contactors of the switches 161 and 171 are changed to terminals of negative positions NP, the switches are on and connect between input side and output side by the reverse phase and the reverse polarity relative to the positive positions PP. Therefore, piezoelectric crystal 601, 602, 60m, are excited positively and negatively through electrodes 801, 901, 801, 902, . . . and 80m, 90m by the electric potential P and provides ultrasonic wave signals to a medium 10. Electric signals generated by the piezoelectric crystal 601, 602 . . . 60m when ultrasonic wave signal are received, are provided to a data processor 4 positively and negatively through the electrodes 801, 901, 802, 902 . . . and 80m, 90m and switches 171, 172, . . . , 17m of the connecting means 17.

Figure 1B:
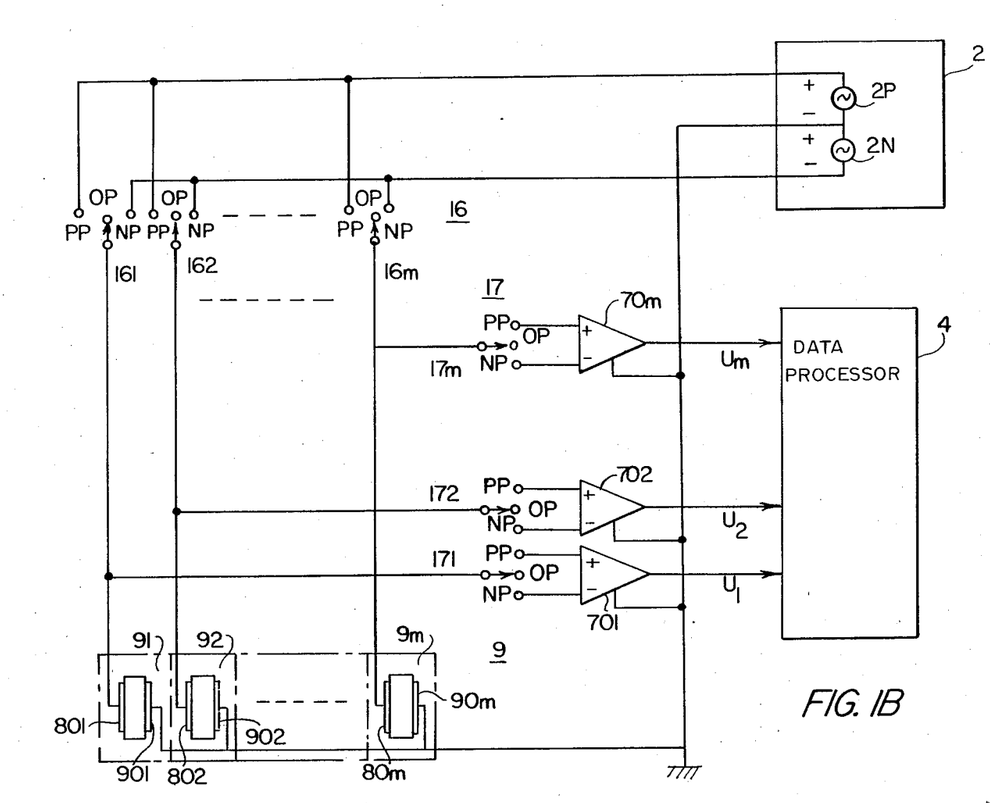
FIG. 1B shows a part of another embodiment of the present invention.

FIG. 1B shows a part of the block diagram of another embodiment of the present invention. In FIG. 1B, each one of two electrodes 801, 802, . . . 80m and 901, 902, . . . 90m of the sending and/or receiving means of the transducer 9 is connected to a common potential point. Each other electrode of the sending, and/or receiving means of the transducer 9 is connected to each contactor of the switches 161, 162, . . . , 16m and switches 171, 172, . . . , 17m, respectively. The electric potential generating means 2 includes two generating means 2P and 2N which generate A.C. electric potential having the same phase, same frequency and same amplitude as shown in FIG. 3A, and which are connected in cascade. The connecting point of the two generating means 2P and 2N is connected to the common potential point too.

The each rest terminal of the electric potential generating means 2P and 2N is connected to each terminal of the positive position PP and the negative position NP of the switches 161, 162, . . . , 16m. Each of polarity changers 701, 702, . . . 70m has two input terminals + and − and a common terminal. The output of the polarity changer is same polarity and same amplitude with an input signal when the input signal is added to the terminal + and is reverse polarity and same amplitude with an input signal when the input signal is added to the terminal −. The common terminal is connected to the common potential point too. Each of the terminals + and − is connected to each of the terminals of a positive position PP and a negative position of switches 171, 172, . . . , 17m.

Figure 3B:
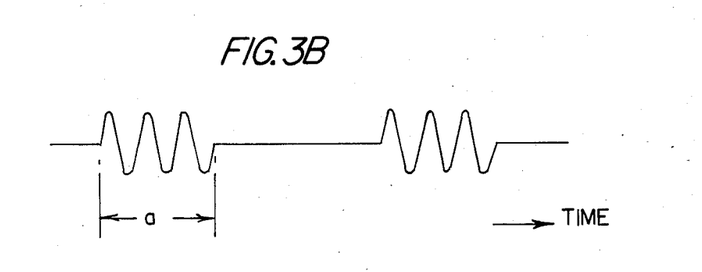

In FIG. 1B, although it needs polarity changers, the switches and circuits are simplified because it uses a common potential point and two electric potential generating means. The control of the connecting means 16 and 17 and the operation of the embodiment are same with that of the embodiment shown in FIG. 1A. A transducer 9 includes m sending and/or receiving means 91, 92, . . . , 9m formed adjacently each other, each of which generates and sends out ultrasonic wave signals when the electric potential is given such wave form as shown in FIG. 3B and each of which generates electric signals when the ultrasonic wave signals are received. The transducer 9 is attached on a medium which may include internal defects 11 in it when an ultrasonic inspection is performed. The data processor 4 has some input lines $U_1, U_2, \ldots U_m$, each of which is respectively connected to each of the corresponding switches of connecting means 17. The data processor processes the electric signals according to a predetermined manner when a data processing control singal DCT is given by the control circuit 1. A display 6 displays figures according to the outputs of the processor 4 and a display control signal DT given by the control circuit 1. An example of the figures on the display 6 is shown as "example of display", in which 71, 72 and 73 show an image of the surface on which the transducer 9 is attached, an image of the bottom surface and a defect image of an internal defect.

The basic construction and operation of the present invention differs with a conventional system in how to provide the electric potential and how to use the electric signals.

Figure 2:
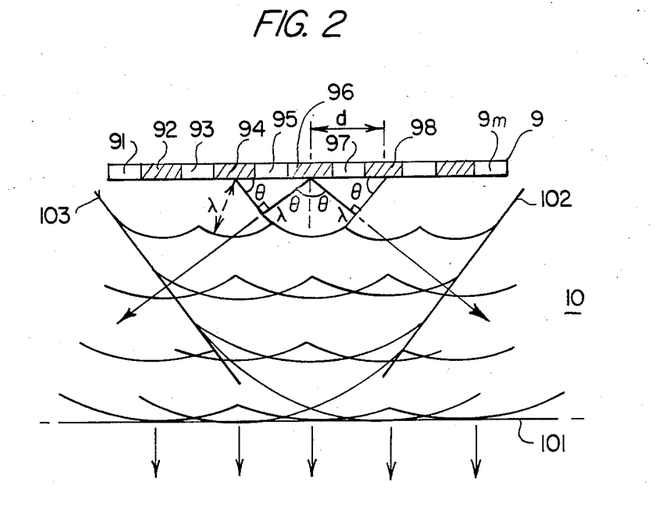
FIG. 2 shows an example of a propagation status of ultrasonic wave signals by the present invention.

FIG. 2 shows an example of a propagation status of ultrasonic wave signals by the present invention. In FIG. 2, transducer 9 includes m sending means of ultrasonic wave signals. Alternate sending means 92, 94, . . . (shown with hatching) are provided the electric potential at same time to send out ultrasonic wave signals. The distance between the adjacent elements which are sending out ultrasonic wave signals is equal and is "d". The wave length of the ultrasonic wave signals generated by the sending element is "λ" which is equal to the period of the A.C. electric potential as shwon in FIG. 3A. In FIG. 3A, the number n of waves of the A.C. electric potential is nearly equal to the number m of sending elements; preferably both are equal. Therefore, ultrasonic wave signals are sent out during of time $a (a = n \times \lambda)$ with wave forms similar to the wave forms of the A.C. electric potential as shwon in FIG. 3B. Further detailed description will be explained below.

In FIG. 2, the selected sending elements 92, 94, . . . send out ultrasonic wave signals with spherical wave. These spherical surface waves interfere, in the medium 10 in front of the transducer 9, with each other and then some wave fronts 101, 102 and 103 are formed. A main lobe which has a wave front 101 is formed in an interference zone towards a direction of angle 0; the angle is measured from the vertical line for the surface sending out ultrasonic wave signals of the transducer 9. Two side lobes which have wave fronts 102 and 103 are formed in interference zones towards a direction of angle θ. The angle θ is defined as follows:

$$\sin\theta = (\lambda/a)\, Tm \quad (1)$$

Figure 4:
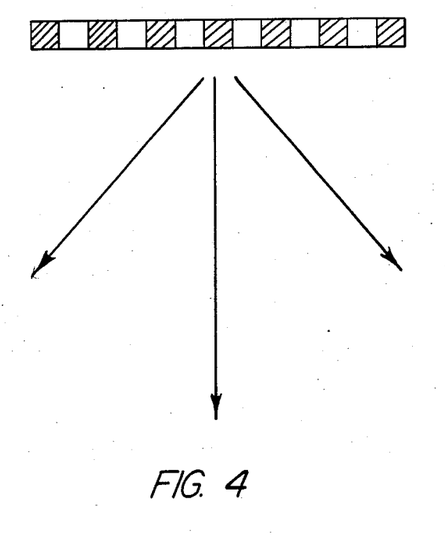
FIG. 4 shows an example of vector components of a propagation of ultrasonic wave signals sent out to a medium.
Figure 5:
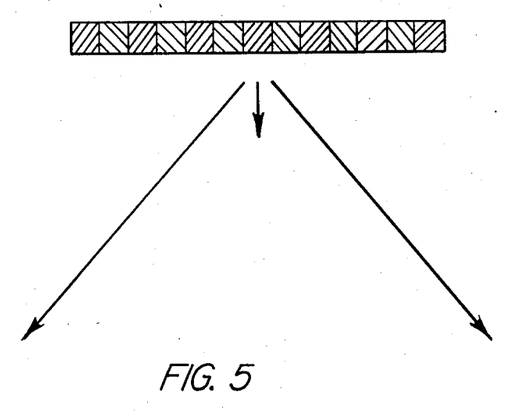
FIG. 5 shows another example of vector components of ultrasonic wave signals sent out to a medium.

As is known from equation (1), θ is a function of the wave length λ of ultrasonic wave signals and the distance d between sending elements being provided the electric potential. This means that ultrasonic wave signals are propagated with direction of a main lobe and two side lobes as shown in FIG. 4. In other words, ultrasonic wave signals are propagated with a characteristic such as vector components. Where the other sending elements 91, 93, . . . which do not satisfy the relation of the equation (1), are provided electric potentials having almost reverse phase, preferably perfect reverse phase, with the A.C. electric potential shown in FIG. 3A, the main lobe formed by the reverse phase A.C. electric potential is formed to delete the main lobe formed by the A.C. electric potential shown in FIG. 3A and the two side lobes formed by the reverse phase A.C. electric potential are formed to add to the two side lobes formed by the FIG. 3A A.C. electric potential. Therefore, if all sending elements are provided the normal and reverse phase A.C. electric potentials the main lobe is deleted almost and two side lobes are amplified about two times as shown in FIG. 5. In FIG. 5 each element having the same hatching line in one direction is provided the same A.C. electric potential and each element having different hatching line is provided reverse phase A.C. electric potential.

Figure 6:
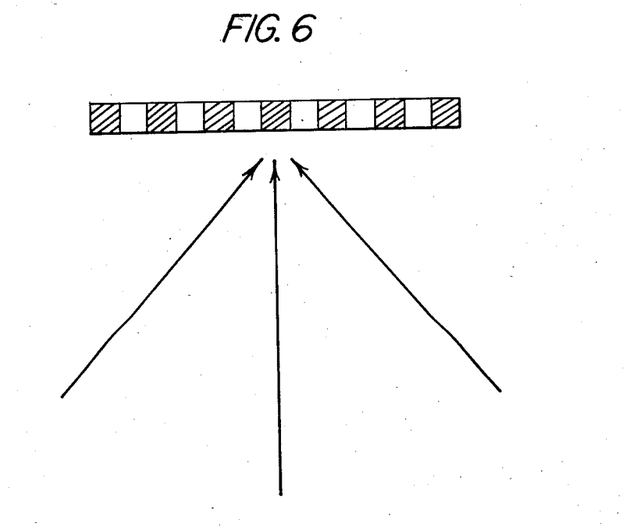
FIG. 6 shows an example of vector components of propagation of ultrasonic wave signals received from a medium.
Figure 7:
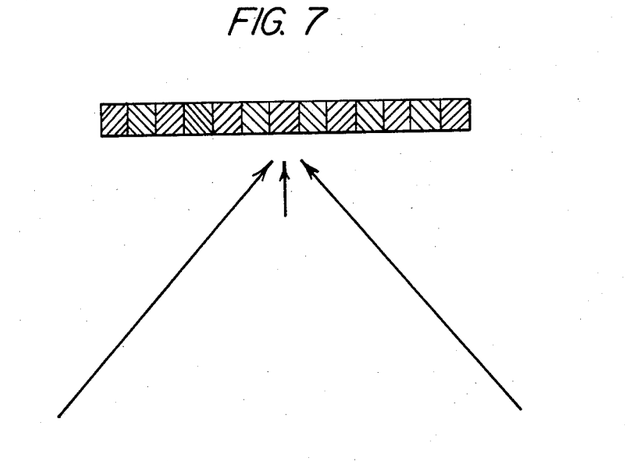
FIG. 7 shows another example of vector components of propagation of ultrasonic wave signals received from a medium.

Ultrasonic wave signals are received by receiving elements of the transducer 9 having the same construction as the sending elements. If output signals generated by the receiving elements, which satisfy the equation (1) between a direction of propagation of ultrasonic wave signals, wave length λ of the ultrasonic wave signals and distance d between the receiving means, are added, the transducer 9 will provide strong receiving signals having the same vector components as such main lobe and two side lobes of the sending ultrasonic wave signals as shown in FIG. 6. Further, if the output signals generated by the receiving elements, which do not satisfy the equation (1), are added with reverse polarity of the outputs of the receiving elements satisfying equation (1), the receiving signals corresponding to the main lobe are deleted almost and the receiving signals corresponding to the side lobes are amplified about two times as shown in FIG. 7. FIG. 6 and FIG. 7 show these status and both figures are corresponding to FIG. 4 and FIG. 5. In both figures, output of each receiving element having same hatching line is added with same polarity and output of each receiving element having different hatching line is added with reverse polarity.

In a view point of a using side lobe of ultrasonic wave signals in the present invention, the main lobe shown in the FIGS. 4 and 6 is an element of an obstruction for a ultrasonic inspection. But it is only a noise element and the idea shown in the FIGS. 4 and 6 are useful for ultrasonic inspection substantially according to the present invention, but the signals of FIGS. 5 and 7 are preferred because they do not have the noise of the main lobe of FIG. 4.

The angle θ of the side lobe is set freely by setting the distance d between the sending elements being provided the electric potential and the distance d between the receiving elements. Therefore, it is only necessary to decide what sending and receiving elements are used. This is very easy to control.

Figure 8:
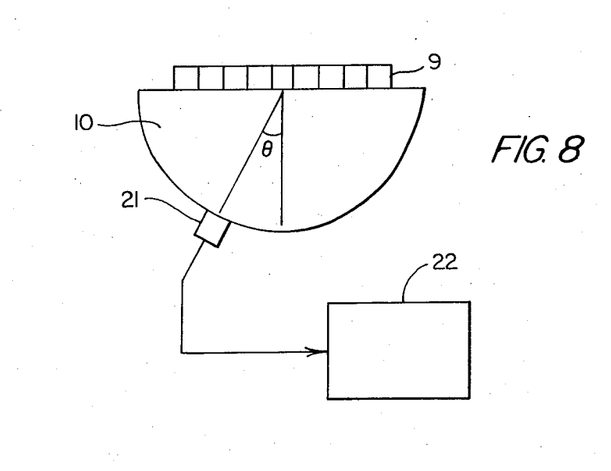
FIG. 8 shows a concept of an experimental device embodying the present invention.
Figure 9:
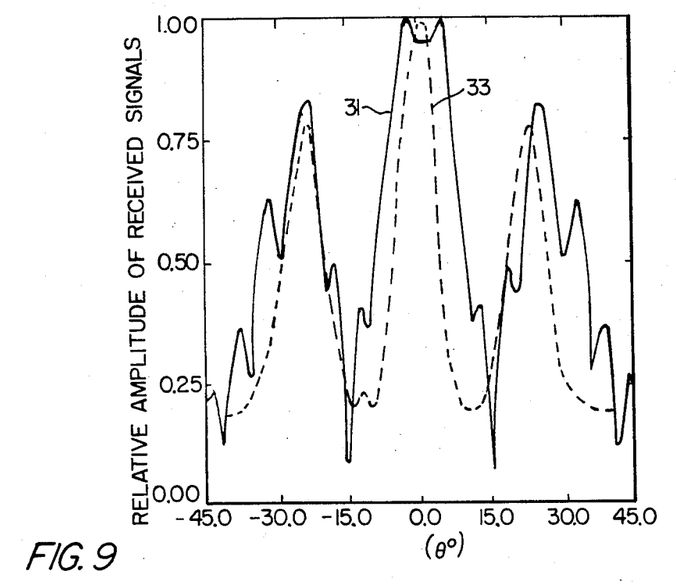
FIG. 9 shows an example of a propagation status of ultrasonic wave signals in a medium.
Figure 10:
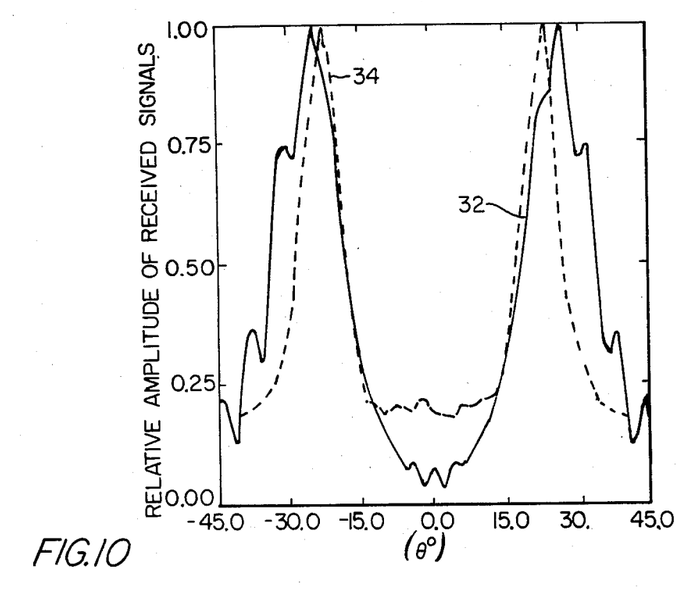
FIG. 10 shows another example of a propagation status.

FIG. 8 shows a concept of an experimental device embodying the present invention. A transducer 9 has some sending elements which are provided A.C. electric potentials as shown in FIG. 4 and FIG. 5. A medium 10 of thin iron has no internal defect and is formed to a semicircle. The transducer 9 is placed on the surface corresponding to the diameter of the semicircle. An ultrasonic wave signal receiving ement 21 is put on the surface corresponding to the circular arc of the semicircle of the medium. An amplitude meter 22 displays the intensity of the ultrasonic wave signals sent out by the transducer 9, propagated in the medium 10 and received by the element 21. FIG. 9 and Fig. 10 show examples of a propagation status of ultrasonic wave signals in the medium 10 as results of experiments and correspond to FIG. 4 and FIG. 5, respectively. In FIG. 9 and FIG. 10, solid lines 31 and 32 show data based on a mathematical analysis and dotted lines 33 and 34 show results of the experiments. The horizontal axis is a refraction angle θ from a vertical line for the surface of the transducer 9. The vertical axis is a relative amplitude of received signals when the peak value of the signal is defined as 1.00. As well shown in FIG. 9 and 10, the side lobes, which are used in the present invention, are gotten with practically full amplitude and sharp narrow width.

Figure 11:
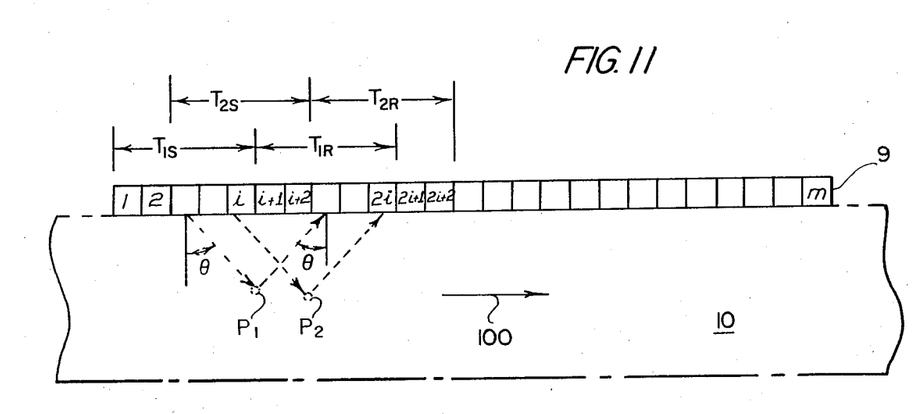
FIGS. 11 to 15 show some applications for ultrasonic inspection of the present invention.

FIGS. 11–FIG. how some applications for ultrasonic inspection of the present invention. More especially, some manners of scan for inspection are described by the FIG. 11–FIG. 15. Transducer 9 having m sending and receiving elements is put on a medium 10.

In FIG. 11, at the first time period $T_1$, the elements from No. 1 to No. i are designated as sending elements and the elements from No. i+1 to No. i+i are designated as receiving elements as shown $T_{1S}$ and $T_{1R}$. The elements within $T_{1S}$ which satisfy the equation (1) are provided an A.C. electric potential to send out ultrasonic wave signal with a refraction angle θ by the switches 16₁, 16₂, ..., 16ᵢ of the connecting means 16. Further, the elements within $T_{IS}$ which do not satisfy the equation (1) are provided a reverse phase A.C. electric potential through the above switches. The outputs of the elements within $T_{1R}$ which satisfy the equation (1) are added to the data processor 4 through the switches $17_{i+1}$, $17_{1+2}$, ..., $17_{i+i}$ of the connecting means 17. Further, the outputs of the element within $T_{IR}$ which do not satisfy the equation (1) are added to the data processor 4 with reverse polarity through the switches $17_{i+1}$, $17_{i+2}$, ..., $17_{i+i}$. In the first time period $T_1$, the position $P_1$ is a target for the inspection. At the second time period $T_2$, the designation of elements as sending and receiving elements are shifted to the right side by two elements as shown $T_{2S}$ and $T_{2R}$. The internal relations of the sending elements and the receiving elements are maintained the same as $T_{1S}$ and $T_{1R}$, respectively. Therefore, in the second time period, the position $P_2$ is a target for the inspection. In this manner, the scan for inspection is performed horizontally as shown by an arrow 100.

Figure 12:
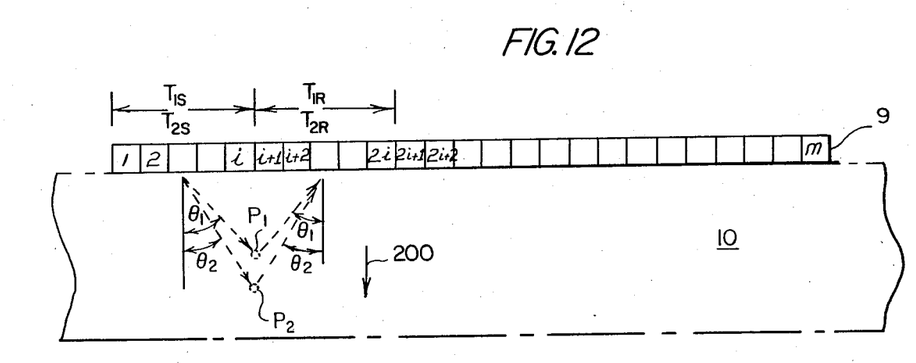

In FIG. 12, at each of time periods $T_1$ and $T_2$, the designations $T_{1S}$, $T_{1R}$ and $T_{2S}$, $T_{2R}$ are maintained the same. But, the internal relations of the sending elements and receiving elements are changed so as to satisfy the equation (1)

$\sin θ_1 = (λα_2)$ at the first time period and $\sin θ_2 = (λα_2)$ at the second time period, respectively.

Namely, in the FIG. 12, the refraction angle θ is changed by changing a distance d of the adjacent selected sending and receiving elements, respectively. In this manner, the scan for inspection is performed vertically as shown by arrow 200.

Figure 13:
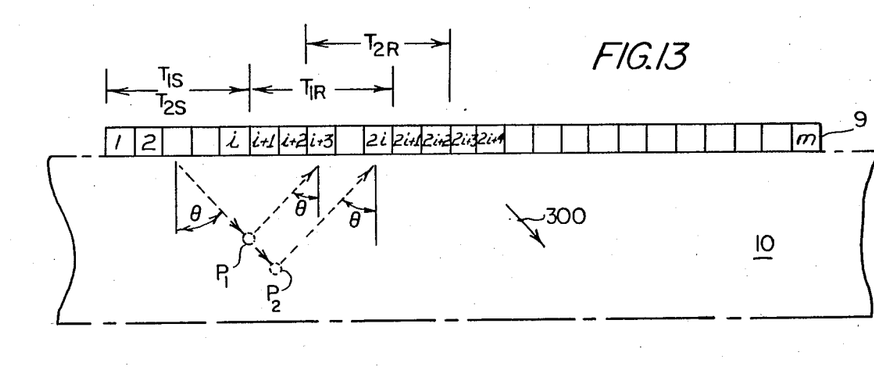

In FIG. 13, the scan for inspection is performed similar to FIG. 11. In FIG. 13, the designation as the sending elements is not changed, but the designation as the receiving elements is shifted at each time period by a predetermined number of elements. The internal relations of the sending elements and the receiving elements are maintained the same as $T_{1S}$ and $T_{1R}$, respectively. In this manner, the scan for inspection is performed slantwise as shown by arrow 300.

Figure 14:
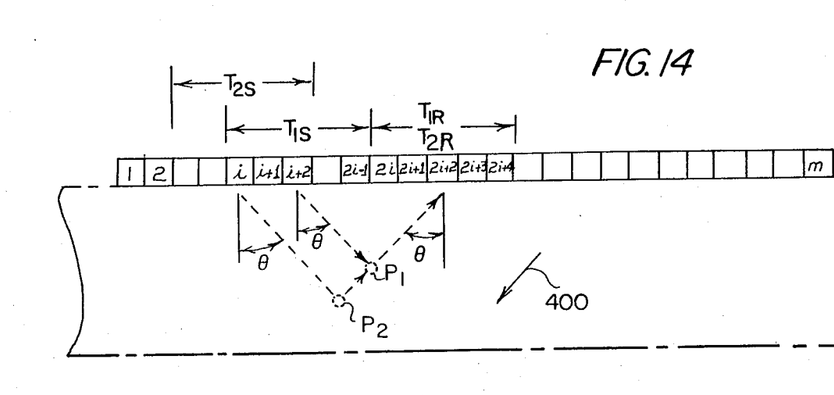

In FIG. 14 the scan for inspection is performed the same manner as FIG. 13 except that the designation as sending elements are shifted and the designation as receiving elements are fixed. Therefore, the scan for inspection is performed slantwise as shown by arrow 400.

Figure 15:
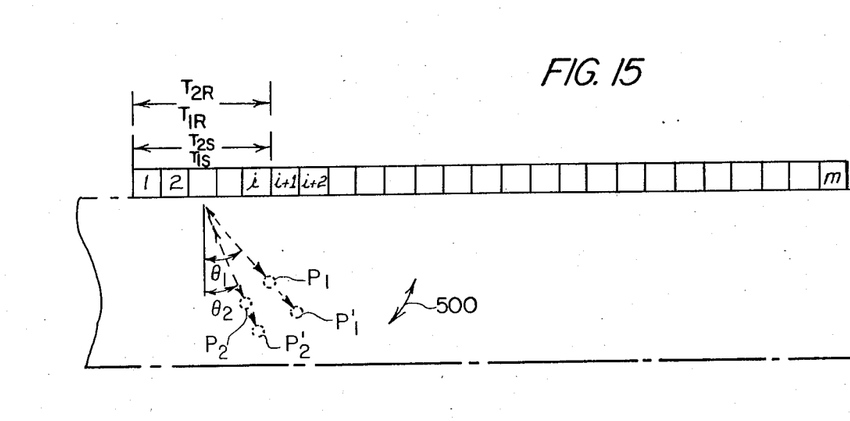

In FIG. 15, the inspection is performed with little difference frm these of FIG. 11–FIG 14. In this case, the same elements are designated as the sending elements and the receiving elements and at each time period, the elements, which satisfy the equation (1), are set as shown in FIG. 12. Since the receiving signals are not available when the ultrasonic wave signals are sending out, the receiving signals are processed by the data processor 4. Therefore, at the first time periods $T_{1S}$, and $T_{1R}$, defects on the line connecting $P_1$–$P_1'$ are detected;

at the second time periods $T_{2S}$ and $T_{2R}$, defects on the line connecting $P_2$-$P_2'$ are detected. In this manner, the scan for inspection is performed along an arc as shown by arrow 500.

Of course, these scans can be combined in order to scan in the medium totally. Further, many other scanning manners are possible from the equation (1). These scanning manner are performed by controlling the connecting means 16, 17 and an operation of the data processor 4 corresponding to the scanning manner.

Figure 16:
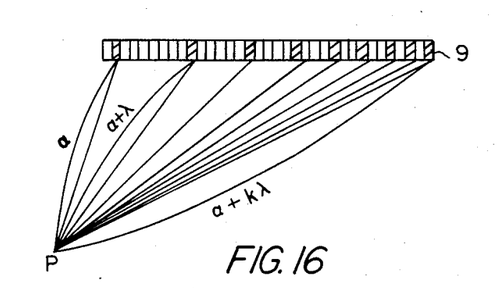
FIGS. 16 to 20 show some variations for the embodiment of the present invention.
Figure 17:
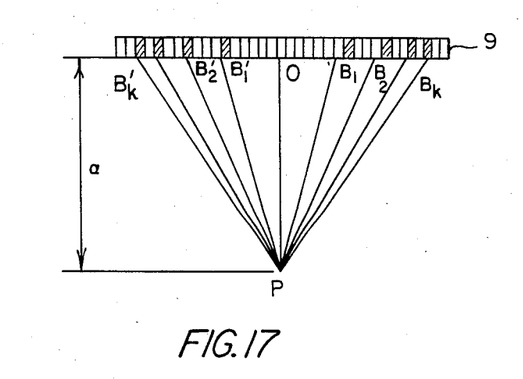
Figure 18:
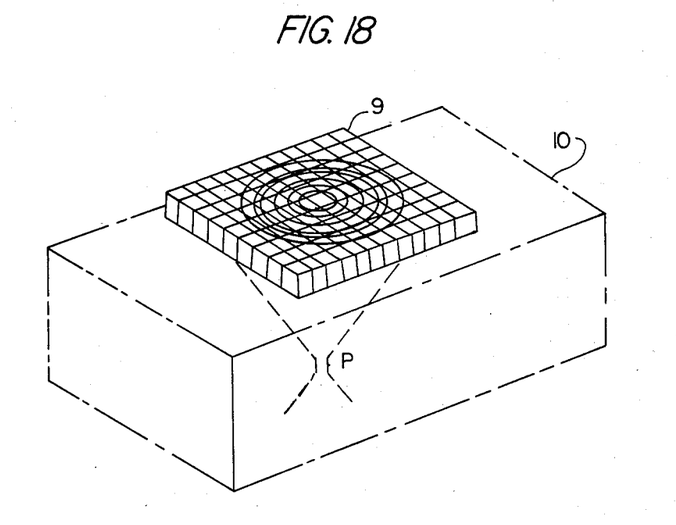

FIGS. 16, 17 and 18 show some different examples to focus ultrasonic wave signals to a point P.

In FIG. 16, elements which satisfy the equation (2) are provided electric potential.

$$L = a + k\lambda \qquad (2)$$

where,
L: distance between element and the point P,
a: ultrasonic wave signal generating period,
λ: wave length of ultrasonic wave signals, and
k: integral number including zero.

In this case, of course, elements which do not satisfy the equation (2) may be provided a reverse phase electric potential in order to eliminate the main lobe of ultrasonic wave signals.

In FIG. 17, elements which satisfy the equation (3) are provided an electric potential. These elements locate on a Fresnel's Ring.

$$L = \sqrt{k \cdot a \cdot \lambda} \qquad (3)$$

where, l, k, a and λ are same with above except k does not include zero.

In this case, of course, elements which do not satisfy the equation (3) and do not locate on Fresnel's Ring are provided a reverse phase electric potential in order to eliminate the main lobe of ultrasonic wave signals.

In FIG. 18, transducer 9 has elements which form a plane having two dimensions. In this case, when each element is provided electric potential with relation shown in FIG. 17, ultrasonic wave signals are focused at point P.

Figure 19:
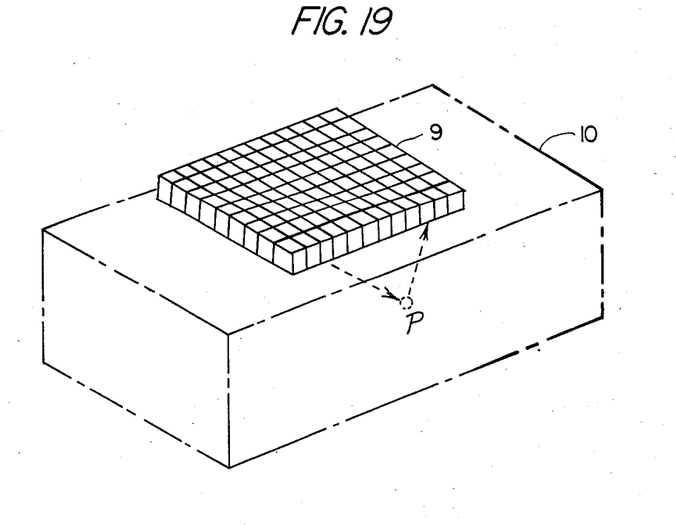

FIG. 19 shows another example about how to use a transducer 9 having a plurality of elements which form a plane. In this case, each row or column is used as shown in FIG. 11 14. Therefore, a broad area is inspected by only controlling the connecting means 16 and 17.

Figure 20:
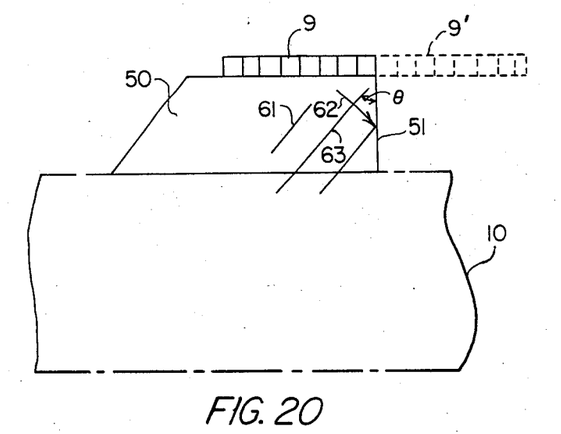

FIG. 20 shows an example which uses an attachment 50 between the transducer 9 and the medium 10. The one end 51 of ends of the attachment 50 has a flat plane aligned with one end of the transducer 9. Therefore, one signal 62 of the ultrasonic wave signals propagating two directions shown by arrows 61 and 62 is reflected by the plane 51 and the reflected signals and signals of director of arrow 61 are made to one side lobe as shown by arrow 63. In this case, the transducer 9 is controlled as shown in FIG. 5, it operates as if another transducer 9' which is shown by dotted line is attached. Therefore, by the example, one side lobe is eliminated and ultrasonic wave signals are propagated to only one direction having a refraction angle θ.

Figure 21:
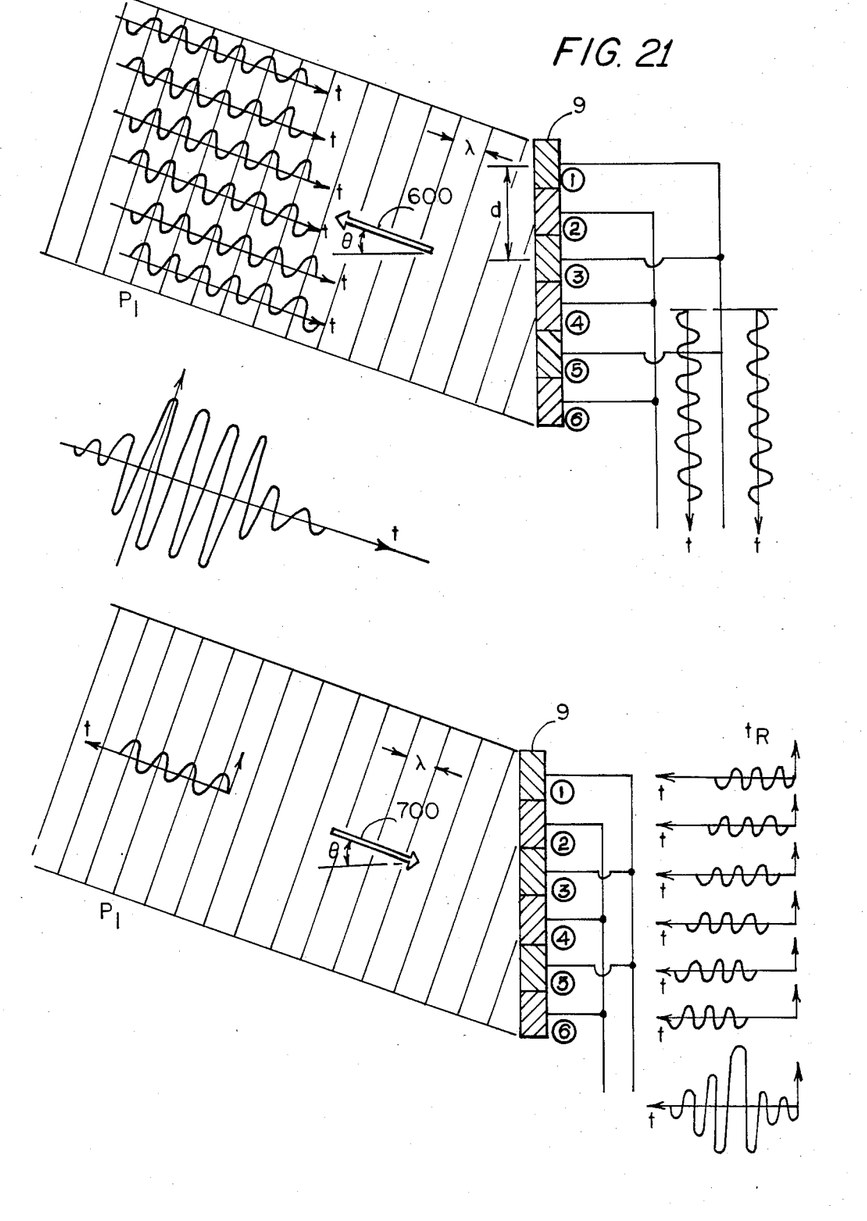
FIG. 21 shows interferences between ultrasonic waves sent out by a plurality of sending means and between electric signals generated by a plurality of receiving means.

In FIG. 21, No. 1, 2, . . . 6, of sending means 9 provide an electric potential with a predetermined phase and with a reverse phase as described before within a period of 6 wave lengths of the electric potential. The ultrasonic wave signals generated by the sending means propagate in the medium 10 to an arrow 600 and interfere at the position $P_1$ which locates the direction satisfying the equation (1) and has a distance of an integral number times wave length λ as shown in the upper portion of FIG. 21. As the result, at the point $P_1$ the amplified ultrasonic wave is obtained as shown in the middle portion of FIG. 21. If there is a defect of the medium at the point $P_1$, the amplified ultrasonic wave is reflected by the defect and propagates towards the receiving means as shown by arrow 700 as shown in the lower portion of FIG. 21. Each receiving means generates an electric signal corresponding to the each arrived ultrasonic signal. The electric signals are added to the signal processor 4 with a predetermined polarity and with a reverse polarity as described before. Therefore, at the time $t_R$, the amplified electric signal by the interference is obtained.

This means that when the sending means is provided the electric potential, at least, for a period of times of number of sending means of wave length λ, the electric signal having the highest amplitude is obtained, because the interferences are occurred at both sending out and receiving the ultrasonic wave signal. In other words, if it is desired to detect a defect being near transducer 9, the period for sending out the ultrasonic wave signal can be reduced by a half number times of sending means of wave length λ, because in this case, at least, at the sending out of ultrasonic wave signals, the interference can be occurred and amplified reflected ultrasonic signals used.

We claim:

1. Apparatus for sending out and receiving ultrasonic wave signals in a medium comprising:
   a plurality of means for sending out the ultrasonic wave signals to the medium when an electric potential having a wave form is given, said plural sending means being aligned in one direction adjacently each other;
   a plurality of means for receiving the ultrasonic wave signal from the medium and for generating corresponding electric signals when the ultrasonic wave signals are received, siad plural receiving means being aligned in one direction adjacently each other;
   means for generating the electric potential;
   means for processing the electric signal generated by said receiving means to display receiving status of the ultrasonic wave signals;
   means for electrically connecting between said electric potential generating means and said plural sending means;
   means for electrically connecting between said processing means and said plural receiving means; and
   means for controlling said two connecting means to form a first connection pattern between some of said plural sending means and said electric potential generating means establishing an acoustic sending side lobe with a first refraction angle and to form a second connection pattern between some of said plural receiving means and said processing means for receiving an acoustic receiving side lobe with a second refraction angle to inspect a portion of the medium at one time and for controlling at least one of said two connecting means so that at least one of the first connection pattern and the second connection pattern is shifted in said one direction and established at a different portion of the respective said plural sending means and plural receiving means at a different time to inspect another portion of the medium.

2. Apparatus for sending out and receiving ultrasonic wave signals in a medium comprising:
- a plurality of means of sending out the ultrasonic wave signals to the medium when an electric potential having a wave form is given, said plural sending means being aligned in one direction adjacently each other;
- a plurality of means for receiving the ultrasonic wave signal from the medium and for generating corresponding electric signals when the ultrasonic wave signals are received, said plural receiving means being aligned in one direction adjacently each other;
- means for generating the electric potential;
- means for processing the electric signals generated by said receiving means to display receiving status of the ultrasonic wave signals;
- means for electrically connecting between said electric potential generating means and said plural sending means;
- means for electrically connecting between said processing means and said plural receiving means; and
- means for controlling said two connecting means to form a first connection pattern between some of said plural sending means and said electrical potential generating means establishing an acoustic sending side lobe with a first refraction angle and to form second connection pattern between some of said plural receiving means and said processing means for receiving an acoustic receiving side lobe with a second refraction angle to inspect a portion of the medium at one time, respectively, and for controlling at least one of said two connecting means to form a corresponding one of a third connection pattern between said some of said plural sending means and said electric potential generating means and a fourth connection pattern between said some of said plural receiving means and said processing means, at a different time to inspect another portion of the medium at a third refraction angle different from said first and second refraction angles.

3. The apparatus according to claim 1, further including means for controlling said two connecting means to establish said first connection pattern between first ones of said some of said plural sending means and said electric potential generating means with a phase and between the rest of said some of said plural sending means and said electric potential generating means with a substantially reverse phase and to establish said second connection pattern between first ones of said some of said plural receiving means and said processing means with a polarity and between the rest of said some of said plural receiving means and said processing means with a substantially reverse polarity.

4. The apparatus according to claim 2, further including means for controlling said two connecting means to establish said first connection pattern between first ones of said some of said plural sending means and said electric potential generating means with a phase and between the rest of said some of said plural sending means and said electric potential generating means with a substantially reverse phase and to establish said second connection pattern between first ones of said some of said plural receiving means and said processing means with a polarity and between the rest of said some of said plural receiving means and said processing means with a substantially reverse polarity.

5. Apparatus for sending out and receiving ultrasonic wave signals in a medium comprising:
- a plurality of means for sending out the ultrasonic wave signals to the medium when an electric potential having a wave form is givne, said plural sending means being aligned in one direction adjacently each other;
- a plurality of means for receiving the ultrasonic wave signal from the medium and for generating corresponding electric signals when the ultrasonic wave signals are received, said plural receiving means being aligned in one direction adjacently each other;
- means for generating the electric potential;
- means for processing the electric signals generated by said receiving means to display receiving status of the ultrasonic wave signals;
- means for electrically connecting between said electric potential generating means and said plural sending means;
- means for electrically connecting between said processing means and said plural receiving means; and
- means for controlling said two connecting means to establish first connection pattern between first ones of some of plural sending means and electric potential generating means with a phase and between the rest of some of plural sending means and electric potential generating means with a substantially reverse phase and to establish second connection pattern between first ones of some of plural receiving means and processing means with a polarity and between the rest of some of plural receiving means and processing means with a substantially reverse polarity.

6. Method for sending out ultrasonic wave signals from a plurality of sending means to a medium comprising:
- generating an alternating electric potential with a phase, and wave length;
- connecting electrically between the plural sending means and the electric potential; and
- sending out the ultrasonic wave signals from a plurality of sending means to the medium, in accordance with the connected electric potential with the plural sending means being aligned in one direction adjacently each other;
- controlling said connecting so that a part of the plural sending means are provided the electric potential and the ultrasonic wave signals are sent out with a deflection angle corresponding to the part of the plural sending means.

7. Method of claim 5, including controlling said connecting so that the rest of the plural sending means are provided the electric potential with the reverse phase so that the ultrasonic wave signals are sent out with side lobes with a refraction angle corresponding to the part of the plural sending means and substantially without a main lobe of the ultrasonic wave signals.

8. An ultrasonic inspection method, comprising:
- providing a linear array of acoustic sending and receiving transducers adjacent a material that may have a defect to be inspected;
- connecting an alternating potential source to some of said sending transducers and a signal processing unit to some of said receiving transducers for transmitting a side lobe of an acoustic wave through the material so that said receiving transducers will send defect signals to said processing unit of a defect at a specific zone in the material;

thereafter automatically changing said connecting of said transducers to move the specific zone in the material to a new location; and thereafter automatically repeating the last step as many times as desired to scan the material.

9. Method for sending out and receiving ultrasonic wave signals in a medium comprising:

sending out the ultrasonic wave signals from a plurality of sending means to the medium, when an electric potential having a wave form is given, the plural sending means being aligned in one direction adjacently each other;

generating the electric potential by an electric potential generating means;

connecting electrically between the plural sending means and the electric potential with a phase;

controlling said connecting so that a part of the plural sending means are provided the electric potential and the ultrasonic wave signals are sent out with a refraction angle corresponding to the part of the plural sending means;

receiving the ultrasonic wave signals from the medium and generating electric signals when the ultrasonic wave signals are received by a plurality of receiving means, the plural receiving means being aligned in one direction adjacently each other;

processing the electric signals by a processing means to display receiving status of the ultrasonic wave signals;

connecting electrically betwen the plural receiving means and the processing means with a polarity; and controlling said connecting so that a part of the plural receiving means provide the electric signals to the processing means and the ultrasonic wave signals are received with high sensitivity for a refraction angle corresponding to the part of the plural receiving means.

10. Method for sending out and receiving ultrasonic wave signals in a medium comprising:

sending out the ultrasonic wave signals from a plurality of sending means to the medium when an electric potential having a wave form is given, the plural sending means being aligned in one direction adjacently each other;

generating the electric potential by an electric potential generating means;

connecting electrically between the plural sending means and the electric potential with a phase and with a substantially reverse phase, selectively;

controlling said connecting so that a part of the plural sending means are provided the electric potential with the phase and the rest of the plural sending means are provided the electric potential with the reverse phase and the ultrasonic wave signals are sent out with a refraction angle corresponding to the part of the plural sending means substantially deleted a main lobe of the ultrasonic wave signals.

11. Apparatus for sending out and receiving ultrasonic wave signals in a medium in accordance with claim 1 comprising:

means for transmitting the ultrasonic wave signals between said plural sending and/or receiving means and the medium having a plane being vertical to a surface formed by said aligned plural sending and/or receiving means at the end thereof.

12. Apparatus for sending out and receiving ultrasonic wave signals in a medium according to claim 1 wherein said plurality of sending and/or receiving means are aligned in two directions adjacently each other.

13. The apparatus according to claim 1, further including means for controlling said electric potential generating means to generate at least for a period of a half number times of the sending means of ultrasonic wave length.

14. The method of claim 6, including controlling the electric potential generating means to generate at least for a period of a half number times of the sending means of ultrasonic wave length.

15. Apparatus for sending out and receiving ultrasonic wave signals in a medium in accordance with claim 2, comprising:

means for transmitting the ultrasonic wave signals between said plural sending and/or receiving means and the medium having a plane being vertical to a surface formed by said aligned plural sending and/or receiving means at the end thereof.

16. Apparatus for sending out and receiving ultrasonic wave signals in a medium in accordance with claim 3, comprising:

means for transmitting the ultrasonic wave signals between said plural sending and/or receiving means and the medium having a plane being vertical to a surface formed by said aligned plural sending and/or receiving means at the end thereof.

17. Apparatus for sending out and receiving ultrasonic wave signals in a medium in accordance with claim 4, comprising:

means for transmitting the ultrasonic wave signals between said plural sending and/or receiving means and the medium having a plane being vertical to a surface formed by said aligned plural sending and/or receiving means at the end thereof.

18. Apparatus for sending out and receiving ultrasonic wave signals in a medium according to claim 2, wherein said plurality of sending and/or receiving means are aligned in two directions adjacently each other.

19. Apparatus for sending out and receiving ultrasonic wave signals in a medium according to claim 3, wherein said plurality of sending and/or receiving means are aligned in two directions adjacently each other.

20. Apparatus for sending out and receiving ultrasonic wave signals in a medium according to claim 4, wherein said plurality of sending and/or receiving means are aligned in two directions adjacently each other.

21. An ultrasonic wave transducing apparatus for transmitting an ultrasonic wave into a medium and receiving an ultrasonic echo from the medium to supply an electric signal in response to the received echo for a data processor for processing a display, comprising:

a transducer array composed of plural transducing elements arranged at least in a straight line;

means for continuously generating an electric potential periodically alternating;

first connecting means for selectively connecting some of the plural transducing elements, designated as transmitting elements, with said electric potential generating means to apply the electric potential to the some of the transmitting elements for a time duration;

second connecting means for selectively connecting some of the plural transducing elements, designated as receiving elements, with the data processor to supply the electric signals in proportion to the echo received by the some of the receiving elements for the data processor;

said data processor having means for adding all the electric signals to form a signal for the display; and control means for generating connecting control siganls for said first and second connecting means for determining a distance between adjacent two among the selected transducing elements in both the transmitting and receiving elements for determining the angle at which the ultrasonic wave is radiated into the medium and the echo thereof is received from the medium, respectively.

22. An ultrasonic wave transducing apparatus as defined in claim 21, wherein the time duration is set to be substantially equal to the product of the period of the electric potential and the number of the transducing elements designated as the transmitting and receiving elements.

23. An ultrasonic wave transducing appratus as defined in claim 21, wherein said first connecting means connects said electric potential generating means with the transducing elements as the transmitting elements such that a first group of the elements, selected from at least every second one of the transmitting elements, and a second group of the elements, interposed between ajacent two of the elements of the first group, are supplied with the electric potentials, the phase of the electric potential applied to the first group of the elements being opposite to that of the electric potential applied to the second group of the elements.

24. An ultrasonic wave transducing apparatus as defined in claim 23, wherein said second connecting means connects the data processor with the transducing elements as the receiving elements, selects outputs of a third group of the elements, including at least every second one of the receiving elements, and selects outputs of a fourth group of the elements, interposed between adjacent two of the elements of the third group, said data processor having means adding inverted outputs of the fourth group to the outputs of the third group.

25. An ultrasonic wave transducing apparatus as defined in claim 21, including means for shifting the combination of the transducing elements designated as the transmitting elements and the receiving elements by a number of the elements every time there is a transmitting and receiving operation, whereby the medium is scanned in the horizontal direction thereof.

26. An ultrasonic wave transducing apparatus as defined in claim 21, including means changing the distance between adjacent two of the elements in both the transmitting elements and the receiving elements every time of the transmitting and receiving operation, whereby the medium is scanned in the vertical direction thereof.

27. An ultrasonic wave transducing appratus as defined in claim 21, wherein some of the transducing elements are fixedly designated as the transmitting elements and including means shifting the combination of the transducing elements designated as the receiving elements by a predetermined number of the elements every time of the transmitting and receiving operation, whereby the medium is scanned slantwise therein.

28. An ultrasonic wave transducing apparatus as defined in claim 21, wherein some of the transducing elements are fixedly designated as the receiving elements and including means shifting the combination of the transducing elements designated as the transmitting elements by a predetermined number of the elements every time of the transmitting and receiving operation, whereby the medium is scanned slantwise therein.

29. An ultrasonic wave transducing apparatus as defined in claim 21, wherein said transducer array is composed of plural transducing elements arranged in two dimensions.

* * * * *